US011562810B2

(12) United States Patent
Ikeguchi et al.

(10) Patent No.: US 11,562,810 B2
(45) Date of Patent: *Jan. 24, 2023

(54) ELECTRONIC DATA DOCUMENT FOR USE IN CLINICAL TRIAL VERIFICATION SYSTEM AND METHOD

(71) Applicants: Edward Ikeguchi, New York, NY (US); James Henderson, Templecombe (GB)

(72) Inventors: Edward Ikeguchi, New York, NY (US); James Henderson, Templecombe (GB)

(73) Assignee: Akyrian Systems LLC, New York, NY (US)

( * ) Notice: Subject to any disclaimer, the term of this patent is extended or adjusted under 35 U.S.C. 154(b) by 392 days.

This patent is subject to a terminal disclaimer.

(21) Appl. No.: 16/919,396

(22) Filed: Jul. 2, 2020

(65) Prior Publication Data
US 2020/0350040 A1    Nov. 5, 2020

Related U.S. Application Data

(63) Continuation of application No. 15/092,152, filed on Apr. 6, 2016, now Pat. No. 10,706,958.
(Continued)

(51) Int. Cl.
*G16H 10/20*    (2018.01)
(52) U.S. Cl.
CPC .................. *G16H 10/20* (2018.01)
(58) Field of Classification Search
CPC ...... G16H 10/20; G16H 80/00; H04L 51/063; H04L 51/212
(Continued)

(56) References Cited

U.S. PATENT DOCUMENTS 6,820,235 B1    11/2004   Bleicher et al.
7,251,609 B1    7/2007    McAlindon et al.
(Continued)

FOREIGN PATENT DOCUMENTS

WO    WO-2005001616 A2 *  1/2005   ........ G06F 17/30011
WO    2013136093 A2       9/2013

OTHER PUBLICATIONS viewcontent.cgi.pdf—Joseph Cooley, Sean Smith, 'Privacy-Preserving Screen Capture: Closing the Loop for Medical Informatics Usability', Dartmouth Digital Commons, Computer Science Technical Reports, pp. 5-8, Jul. 2, 2012 (Year: 2012).*
(Continued)

*Primary Examiner* — Rachelle L Reichert
*Assistant Examiner* — Teresa S Williams
(74) *Attorney, Agent, or Firm* — Danielle C. Sullivan; Carter Ledyard & Milburn LLP

(57) ABSTRACT

The present invention provides an electronic data document (EDD) and related system and method for use in a computerized clinical trial verification system. In an exemplary embodiment, the EDD is authenticated by the creator and validated by the receiver, and comprises an image of a source document (SD) that comprises a masked record of at least one interaction between a clinical trial investigator and a patient enrolled in a clinical trial, at least one revealed portion of the SD that includes evidence relevant to at least one question in a clinical trial questionnaire, and at least one annotation connecting the revealed portion to the at least one question. The present invention provides a computerized system and method for allowing a clinical trial investigator to answer questions from a clinical trial questionnaire pertinent to a clinical trial of a medical treatment using encrypted and partially masked electronic documents comprising images of original patient records. The process of
(Continued)

creating and viewing the partially masked electronic documents preferably does not create local copies that can be recalled later.

12 Claims, 13 Drawing Sheets

Related U.S. Application Data

(60) Provisional application No. 62/257,974, filed on Nov. 20, 2015.

(58) Field of Classification Search
USPC .............................................................. 705/2
See application file for complete search history.

(56) References Cited

U.S. PATENT DOCUMENTS

| | | | |
|---|---|---|---|
| 7,349,947 B1 | 3/2008 | Slage et al. | |
| 7,519,591 B2 | 4/2009 | Landi et al. | |
| 7,669,114 B2 * | 2/2010 | Wood | G06F 40/10 |
| | | | 715/255 |
| 7,711,580 B1 | 5/2010 | Hudson | |
| 7,870,006 B2 | 1/2011 | Tkaczyk et al. | |
| 8,452,619 B2 | 5/2013 | Kenedy et al. | |
| 8,504,380 B2 | 8/2013 | Broverman et al. | |
| 8,590,034 B2 | 11/2013 | Hussain et al. | |
| 8,688,475 B2 | 4/2014 | Ferguson | |
| 8,788,285 B2 | 7/2014 | Kuo | |
| 8,904,554 B2 | 12/2014 | Shelton | |
| 9,171,182 B2 | 10/2015 | Shukla et al. | |
| 2002/0035486 A1 | 3/2002 | Huyn et al. | |
| 2008/0290168 A1 | 11/2008 | Sullivan et al. | |
| 2011/0238768 A1 | 9/2011 | Habets et al. | |
| 2011/0239113 A1 | 9/2011 | Hung et al. | |
| 2012/0096005 A1 | 4/2012 | O'Connor | |
| 2012/0221589 A1 | 8/2012 | Shahar et al. | |
| 2012/0245926 A1 | 9/2012 | Montyne et al. | |
| 2013/0041677 A1 | 2/2013 | Nusimow et al. | |
| 2013/0096986 A1 | 4/2013 | Pavagadhi | |
| 2013/0304504 A1 | 11/2013 | Powell | |
| 2013/0304542 A1 | 11/2013 | Powell | |
| 2014/0222444 A1 | 8/2014 | Cierello et al. | |
| 2014/0244296 A1 | 8/2014 | Linn et al. | |
| 2014/0278498 A1 | 9/2014 | Fahimi et al. | |
| 2014/0280376 A1 | 9/2014 | Kuo | |
| 2015/0213235 A1 | 7/2015 | Thiers et al. | |
| 2015/0278444 A1 | 10/2015 | Westin et al. | |
| 2016/0147963 A1 | 5/2016 | Bouhnick | |

OTHER PUBLICATIONS

Cooley J., Smith S., "Privacy-Preserving Screen Capture: Towards Closing the Loop of Health IT Usability," Journal of Biomedical Informatics, 2013, pp. 721-733, vol. 46, Elsevier, USA.

Cooley J., Smith S., "Privacy-Preserving Screen Capture: Closing the Loop for Medical Informatics Usability," Dartmouth Computer Science Technical Report TR2012-725, 2012, pp. 1-35, Dartmouth College, Hanover, USA.

Cooley J., "Screen Capture for Sensitive Systems," Dartmouth Computer Science Technical Report TR2011-690, 2011, pp. 1-128, Dartmouth College, Hanover, USA.

Abril et al., "On the Declassification of Confidential Documents," 2011, pp. 235-246, 8th International Conference on Modeling Decisions for Artificial Intelligence.

Cumby et al., "A Machine Learning Based System for Semi-Automatically Redacting Documents," 2011, pp. 1628-1635, Proceedings of the 23rd Innovative Applications of Artificial Intelligence Conference.

Chakaravathy et al., "Efficient Techniques for Document Sanitization," 2008, pp. 843-852, Proceedings of the 17th ACM Conference on Information and Knowledge Management.

* cited by examiner

FIG. 2

ELECTRONIC DATA DOCUMENT FOR USE IN CLINICAL TRIAL VERIFICATION SYSTEM AND METHOD

This application is a Continuation of U.S. patent application Ser. No. 15/092,152 filed Apr. 6, 2016, which issued as U.S. Pat. No. 10,706,958 on Jul. 7, 2020, and claims priority to U.S. Provisional Patent Application No. 62/257,974 filed Nov. 20, 2015 entitled "Clinical Trial Source Document Verification System And Method" all of which are hereby incorporated by reference in their entirety.

This idea pertains to the field of clinical research, in which experimentation is conducted upon human beings in order to assess the safety and efficacy of new medical treatments. The time required for a new compound to go from discovery to market is approximately 12 years, with as much as half that time spent in clinical trial testing. It is estimated that only one out of every 5000 newly discovered compounds ever reach the market. It is important for pharmaceutical companies to be able to ascertain not only which drugs will succeed, but also which drugs will fail the rigors of experimentation as quickly as possible. In addition, since the timeframe for patent protection begins when a new compound is discovered and patent protection is sought, each day lost in the clinical trial process may be time lost in the period when a drug can be marketed under patent protection.

The process of data collection for a clinical trial begins with an interaction between a physician (the Investigator) and a patient (the Subject). This interaction is documented in writing in the patient's medical record and considered to be a legal document. The medical record consists primarily of alphanumeric characters written by the physician to describe the interaction with the patient and is considered to be the first moment in time when a record is created: this is referred to as the Source Document (SD). The physician records information in the SD about the patient's complaints, prior conditions, medications, allergies, physical examination findings, lab tests, imaging tests, and plan, for example. For purposes of clinical research, however, only a subset of the information in the SD is needed. For example, a clinical trial about hypertension might only require information about blood pressure, and even though the SD might also contain information written by the doctor about the patient's prostate exam, only the blood pressure needs to be extracted as relevant data from the SD.

Manufacturers of medical treatments will frequently recruit the help of Investigators to conduct clinical studies. These manufacturers are known as Sponsors. Sponsors will create forms (also known as a case report form or CRF) that should be filled out by the Investigators and/or their hospital staff. The CRF contains questions about the Subject relevant to the clinical trial. Answers to these questions must be submitted by the Investigator in order for the Sponsor to gather data about the efficacy and safety of their medical treatment. Until recently, the CRF has been a paper document, completed by the Investigator using their own handwriting. Upon completion of the CRF, the Investigator transmits the CRF to the Sponsor, usually by fax or by mailing copies. Upon receipt of the CRF, the Sponsor then transcribes information from the CRF into a database. Since this transcription process is a point for potential human error, Sponsors will often enter the data twice and later reconcile any errors of transcription. This process is known as double data entry (DDE).

It is recognized that another potential step that may lead to human error is the process in which information is transcribed by the Investigator or their staff from the SD into the CRF. In order to minimize this potential for error, Sponsors perform a process in which the information written on the CRF is checked against the information in the SD. This process is known as Source Document Verification (SDV). In practice, this requires personnel representing the Sponsor to carry the CRF to the medical office of the Investigator in order to view the SD and perform a comparison. This process is very tedious, time-consuming, and requires much traveling and cost.

Over the past two decades, the industry has adopted a new technology to enable a CRF to be presented to an Investigator in an electronic form. The electronic CRF (or eCRF) is typically a web-based form viewed via a computer with areas of text representing questions followed by any one of a variety of mechanisms to allow the Investigator to submit answers: open text fields, radio buttons, drop-down menus, etc. However, the process of filling out an online form representing an eCRF is still performed by the Investigator referencing the patient chart (SD). Therefore, this continues to be a transcription process and subject to human error. Therefore, even using eCRF, there is still a need for the Sponsor to perform quality control checks through SDV.

There are advantages to using an eCRF, however, because there is no longer a need for paper forms to be faxed between Investigator and Sponsor, and electronic forms are more legible than handwritten forms. Also, eCRF's can be programmed so that potential errors may be flagged by the eCRF at the time of data entry. For example, if an Investigator enters a heart rate value of 800, an eCRF can be programmed with computer code to detect when the entered value is out of range. Such computer code is referred to as an Edit Check. In this example, an Edit Check could be used to alert the Investigator that the heart rate of 800 is out of range. The Investigator would be able to immediately react to the problematic data and make a correction. If a paper CRF were being used, this same example would lead to many days lost in the data cleaning process for the clinical trial because the doctor might not notice the error, the paper CRF would be faxed to the Sponsor, the erroneous data would be entered into a database, and many days to weeks later, an Edit Check would be programmed and applied at the database level to flag the data as out-of-range.

These flags raised for problematic data are known as Queries. A report of this Query would then have to be printed and faxed back to the Investigator who would try to resolve the Query by referencing back to the SD. This process of cleaning data is time consuming for any clinical trial, and generally adds weeks to months, and even years of time to the drug development cycle. While the use of an eCRF can save some time in the data cleaning process, significant time and expense is still incurred in the process of programming Edit Checks. To sum, whether a Sponsor uses a paper CRF or an eCRF, there are many weeks to months spent by data management personnel to program edit checks for each question of a CRF. Also, the process of transcribing information from a SD to CRF (or eCRF) is still a point of potential human error, and therefore still requires the Sponsor to perform SDV.

One prior art process for verifying clinical trial source data is described in U.S. Patent Application Publication US 2012/0096005 to O'Conner and partially described in FIG. 1. Specifically, this prior art technique, inter alia, electronically acquires images of source documents, indexes the images and stores the images in a source database in a predetermined order based on the indexing, selects an image from the source database, interfaces with a clinical database, and simultaneously displays data from the clinical database alongside the selected image in a clinical research setting, as further described therein. However, this prior art technique still requires the Investigator or a nurse to manually transcribe information from the SD to the eCRF, and does not provide reliable data accountability, Investigator verification of answers to the eCRF, or strong protections for patient privacy.

In addition, pharmaceutical companies tend to keep their data transfer systems and informatics systems proprietary since they do not want research data to go easily outside of their own corporate firewalls. Thus, computer systems and informatics systems of pharmaceutical companies are not easily "plugged into" hospital systems. Thus, there exists a need to safely and confidentially transmit and verify original patient data recorded in hospital systems and to provide a convenient and reliable way that complies with patient privacy restrictions to provide necessary clinical trial data to informatics systems of pharmaceutical companies which have engaged such hospital systems to participate in clinical trials for medical treatments developed by the companies.

SUMMARY OF THE INVENTION

The present invention provides an electronic data document (EDD) for use in a computerized clinical trial verification system. In an exemplary embodiment, the EDD includes (1) first computer instructions associated with the EDD that permit a receiver of the EDD to validate a sender of the EDD and an electronic data structure of the EDD, (2) an image of a source document (SD) that comprises a record of at least one interaction between a clinical trial investigator and a patient enrolled in a clinical trial, (3) at least one revealed portion of the SD that comprises evidence relevant to at least one question in a clinical trial questionnaire, and (4) at least one marking connecting the revealed portion to the at least one question.

In a further embodiment, the EDD further includes second computer instructions associated with the EDD that mask all portions of the SD not included in the revealed portion and that permit authorized persons to selectively unmask one or more portions of the SD that are not included in the revealed portion. In a further embodiment, the EDD further includes third computer instructions that permit one or more authorized persons to accept the revealed portion as sufficient evidence to answer the at least one question.

In an exemplary embodiment, the EDD is encrypted. In a further embodiment, the EDD further includes fourth computer instructions that permit the investigator to associate an electronic signature with the EDD, thereby allowing the investigator to note that the EDD is truthful and representative of the patient, dates, and information submitted in response to the clinical trial questionnaire. In a further embodiment, the EDD further includes fifth computer instructions that permit the investigator to associate an electronic signature with the revealed portion, thereby allowing the investigator to note that the revealed portion is truthful and representative of the patient and of dates associated with the revealed portion. In a further preferred embodiment, the EDD is not saved as a file that can be recalled at a later time.

The present invention provides a computerized system and method for allowing at least one medical professional (Investigator) to answer questions from a clinical trial questionnaire (case report form (CRF)) pertinent to a clinical trial of a medical treatment. In an exemplary embodiment, the system includes (1) a source document (SD) ingester configured to allow the Investigator to answer the questions with digital images of portions of the SD (SD revealed portions or snippets) as evidence for answers to the questions, where the SD includes a description of at least one interaction between the Investigator and a patient enrolled in the clinical trial (Subject), (2) a SD snippet markup tool configured to allow the Investigator to annotate the SD snippets, thereby allowing the Investigator to draw attention of the Sponsor to information relevant to the clinical trial via annotated SD snippets, (3) a sponsor viewing tool configured to allow a manufacturer of the medical treatment (Sponsor) to view the SD snippets and the marked SD snippets, and (4) a reviewing tool configured to allow the Sponsor to accept the SD snippet images if the SD snippet images are supportive or are representative of the answers to the questions and to reject the SD snippet images if the SD snippet images are not supportive or are not representative of the answers to the questions.

In an exemplary embodiment, the sponsor viewing tool is configured to be responsive to computer instructions that mask from viewing by the Sponsor all portions of the SD that do not correspond to the SD snippet images. In a further embodiment, the sponsor viewing tool is further configured to display to at least one authorized person at least one portion of the SD that does not correspond to the SD snippet images. In a further preferred embodiment, the sponsor viewing tool does not create any local or temporary copies of the SD or any portions thereof.

In a further embodiment, the SD ingester is further configured to allow the Investigator to capture a digital image of the entire SD (SD full image). In a further embodiment, the SD ingester further associates computer instructions with the SD full range that mask the SD full image and also are configured to display to at least one authorized person the SD full image. In a further preferred embodiment, the SD ingester does not create any local or temporary copies of the SD image.

In a further embodiment, the system further includes an electronic signature tool configured to allow the Investigator to associate an electronic signature with the SD snippet images, thereby allowing the Investigator to note that the SD snippet images are truthful and representative of the Subject, dates, and information submitted in response to the CRF. In a further embodiment, the SD ingester further includes an electronic signature tool configured to allow the Investigator to associate an electronic signature with the SD full image, thereby allowing the Investigator to note that the SD full image is truthful and representative of the Subject, dates, and information submitted in response to the CRF.

BRIEF DESCRIPTION OF THE DRAWINGS

FIG. 2 is a diagram of a user interaction in accordance with an exemplary embodiment of the present invention.

DESCRIPTION OF THE INVENTION

Figure 1:
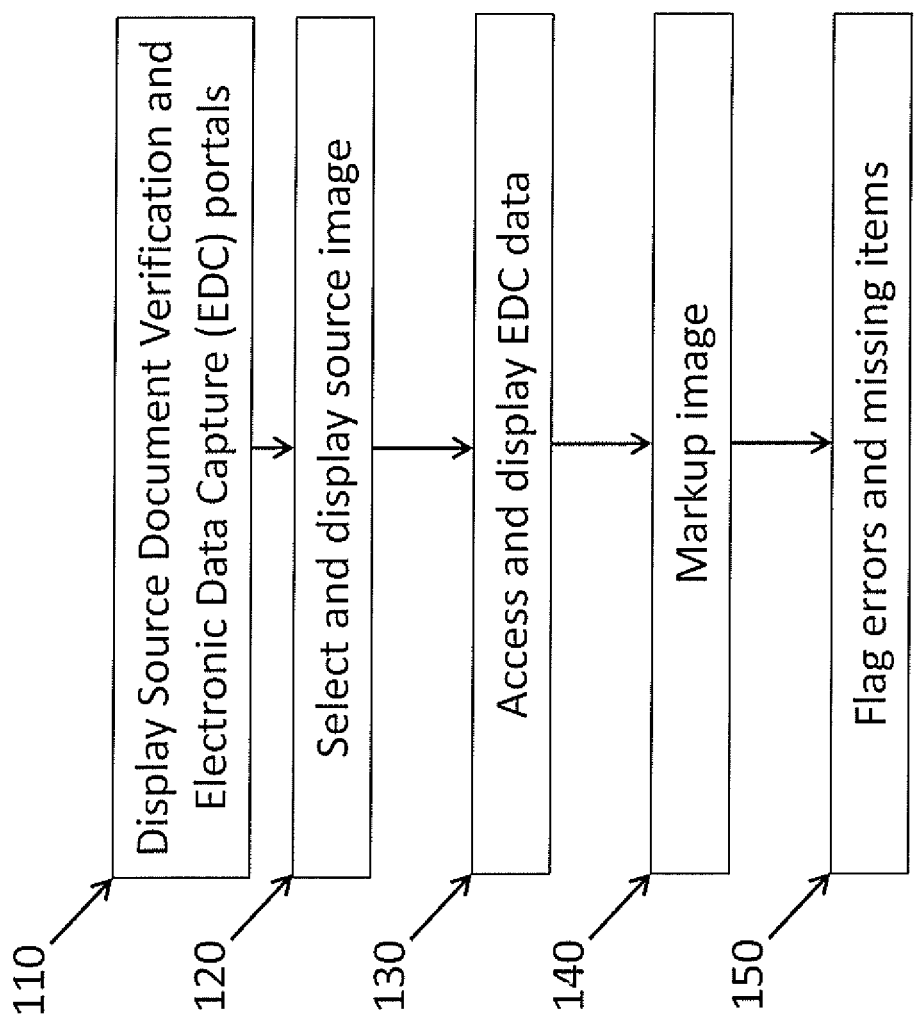
FIG. 1 is a flowchart of a prior art technique.

This invention provides a means of allowing Investigators to provide Sponsors with SD image sections (snippets) corresponding to the answers to questions posed by the eCRF. Since the eCRF questions are being answered by images coming directly from the SD, it is no longer a transcription process, and therefore obviates the need to perform SDV. Also, since the SD is the ultimate resource of original data, there is virtually no need for programming edit checks to evaluate the quality of the data or to do other time consuming data cleaning. The SD is considered to be a legal document and the information in it is considered to be final. Also, in modern times, most doctor's offices and hospitals have adopted electronic medical records (EMR) and these systems already contain complex error-checking programming. This invention enables Sponsors to leverage the error-checking that already exists in EMR systems.

The current idea presents a process in which the Sponsor is able to perform single or double data entry directly from relevant portions of the SD, thus skipping the step where the Investigator fills out the CRF with alphanumeric data. The invention involves a method in which the Investigator fills out the CRF with images of select portions of the SD where the relevant alphanumeric information is visible. The SD images can be obtained by a digital camera for paper source documents or the screen-capture capability within software for electronic SD. In order to protect patient privacy as required by the Health Insurance Portability and Accountability Act (HIPAA), FDA Title 21 CFR Part 11, and other laws and regulations, and to direct the Sponsor's attention to only the relevant information, the Investigator is able to mark the images with drawing and labeling tools. Also, to protect patient privacy, areas that are not marked by the Investigator are made invisible to the Sponsor by electronic masking such that the sponsor may see only the alphanumeric information on the images that the Investigator decides are relevant and responsive to the clinical trial.

Since the Investigator is no longer filling out a form, but rather, marking images taken from the original SD, there is no longer a risk for transcription error. Since the Sponsor is viewing an exact digital image of the section of the SD needed for the clinical study, single or double data entry is performed directly from an image of the SD, and therefore eliminates or greatly reduces the need to perform in person SD verification.

The invention is a computer-implemented system and method for collecting clinical research data, utilized, inter alia, by a pharmaceutical company or a medical device company for data entry and verification of data. Currently, pharmaceutical companies send representatives to medical offices where the representative physically cross-checks the pharmaceutical company's record with the medical records of the medical office, entering study-relevant data from the medical records into the pharmaceutical company's database and correcting erroneous entries. This process is inefficient and expensive. Proposed solutions for sharing the patient record information online by giving the Sponsor direct access to all of the Investigator's electronic medical records raise privacy concerns—thus, the representative must physically go to the medical office and will likely have to go through many paper and electronic documents to find the relevant information. The present invention offers a solution to sharing such information without requiring travel and without providing the pharmaceutical company unfettered access to a patient's full medical record containing confidential patient information.

The present invention may be implemented by a physician or nurse taking a screen shot of a page (or snap shot of a particular section on a page), labeling that screen shot to identify the relevant data it contains (e.g., temperature, blood pressure, etc.), and adding any comments relating to the data or its application to a clinical study to that screen shot. Thus, without having to enter patient information into a new form, the doctor or nurse can identify information generally relevant to studies that might be performed by various pharmaceutical companies. Similarly, a physician or nurse may take a photo (e.g., with a smart phone app) of paper test records unavailable on a computer, label that information with or without comment, and electronically include such test records using the same program. The patient information that is not selected/labeled by the physician is electronically redacted, thus allowing only study-relevant material to be shared electronically with the pharmaceutical company. The company receives this information in a manner such that only the portions of the record that are labeled by the medical office are shown, either surrounded by redacted portions of the SD or alternatively showing just the relevant data in each snap shot, one by one. This, in turn, shows the pharmaceutical company all the data it needs to see and none of the information that is irrelevant to the study and/or raises privacy issues. Because the sections of a medical record are selected and labeled by the medical office, the pharmaceutical company can determine what information it wants to see on a study-by-study basis using a Clinical Research Form and the present invention will provide that information. This will save the pharmaceutical company time in having to review an entire medical file to verify the information. And the information can be shared electronically without raising privacy concerns because only study-relevant information can be viewed by the Sponsor's reviewers.

Furthermore, if redacted portions of the medical file need to be reviewed for regulatory or fraud elimination purposes (e.g., by an FDA auditor, or a high-level executive of the Sponsor company), a user with the proper authorization is able to view the redacted information in a limited but sufficient manner (e.g., a viewport). Thus, the invention masks the confidential information from general view but retains the data of that information as part of the redacted SD in case an authorized person needs to view it to, e.g., confirm that the data being shared is in fact related to a particular patient.

Figure 2:
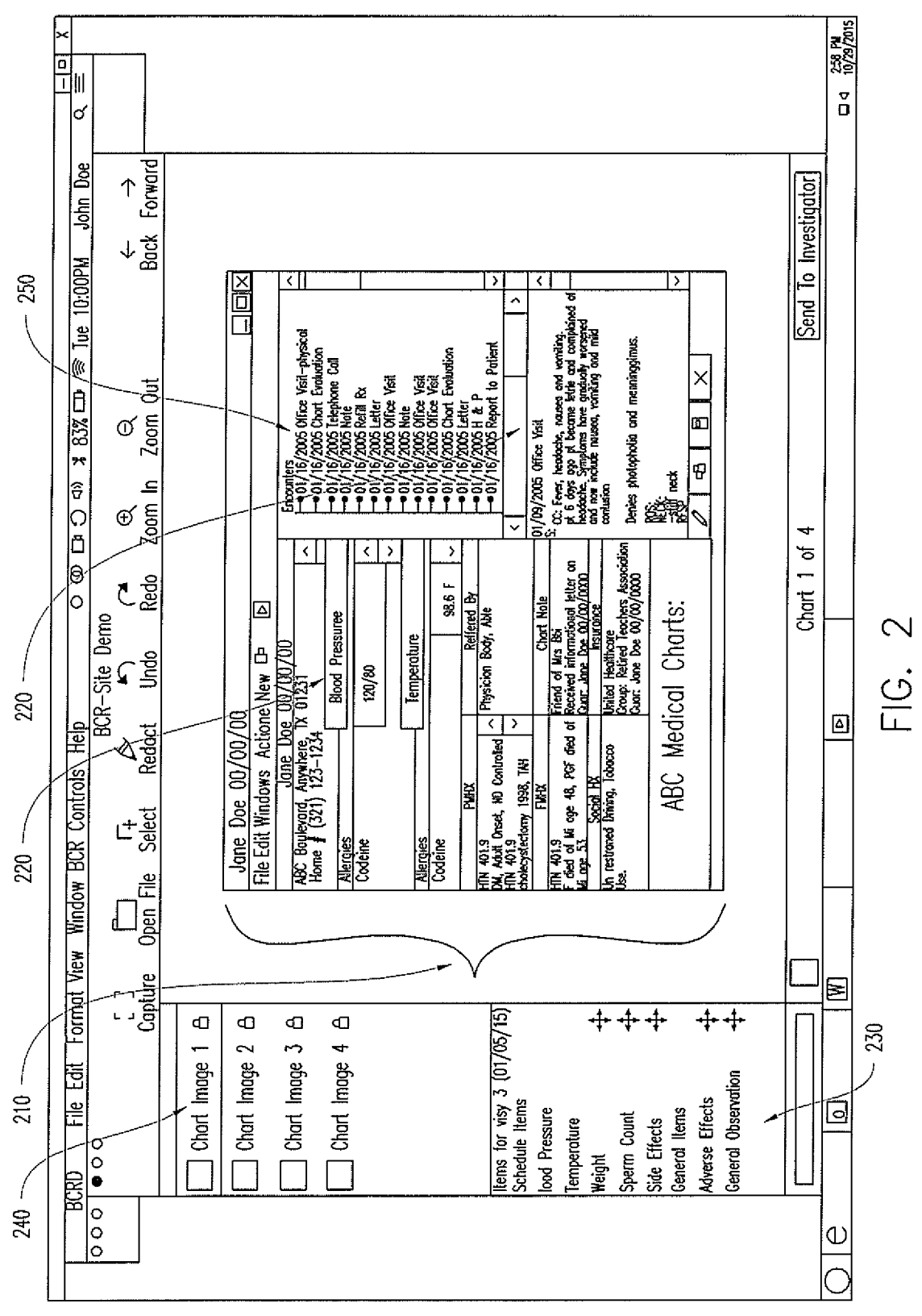

Referring to FIG. 2, in an exemplary embodiment, the present invention allows a physician (Investigator) or nurse to select particular data 220 and label it from a complete medical record 210. The present invention allows the Investigator to use additional labels 230 as well. The Investigator may select particular portions 220 (i.e., captures) of the medical record via the invention, including any scanned paper charts, and add them as chart images 240. The patient's prior interactions history 250 is also available for use by the Investigator to select to add as a chart image.

Figure 3:
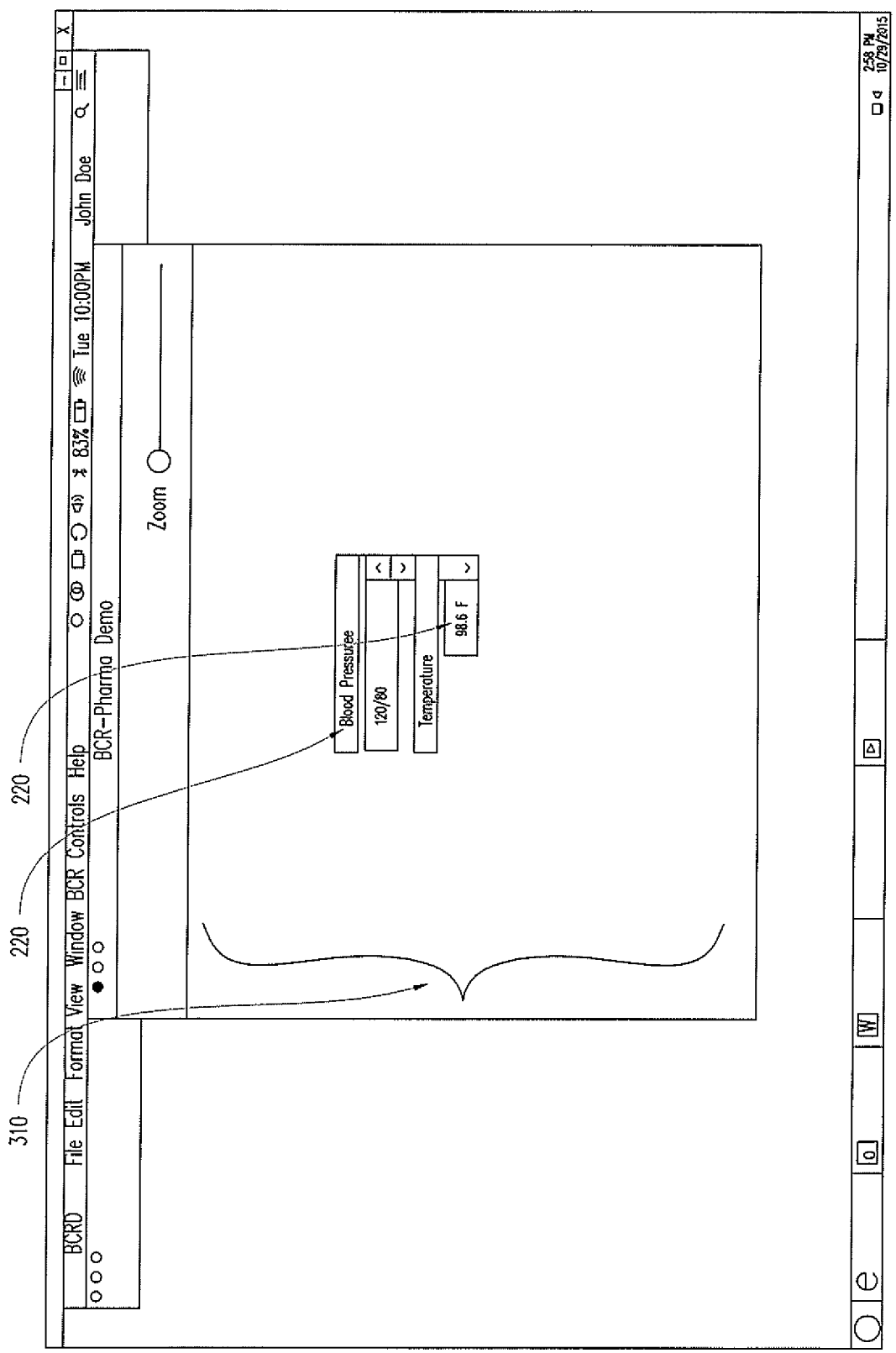
FIG. 3 is a diagram of a user interaction in accordance with an exemplary embodiment of the present invention.
Figure 4:
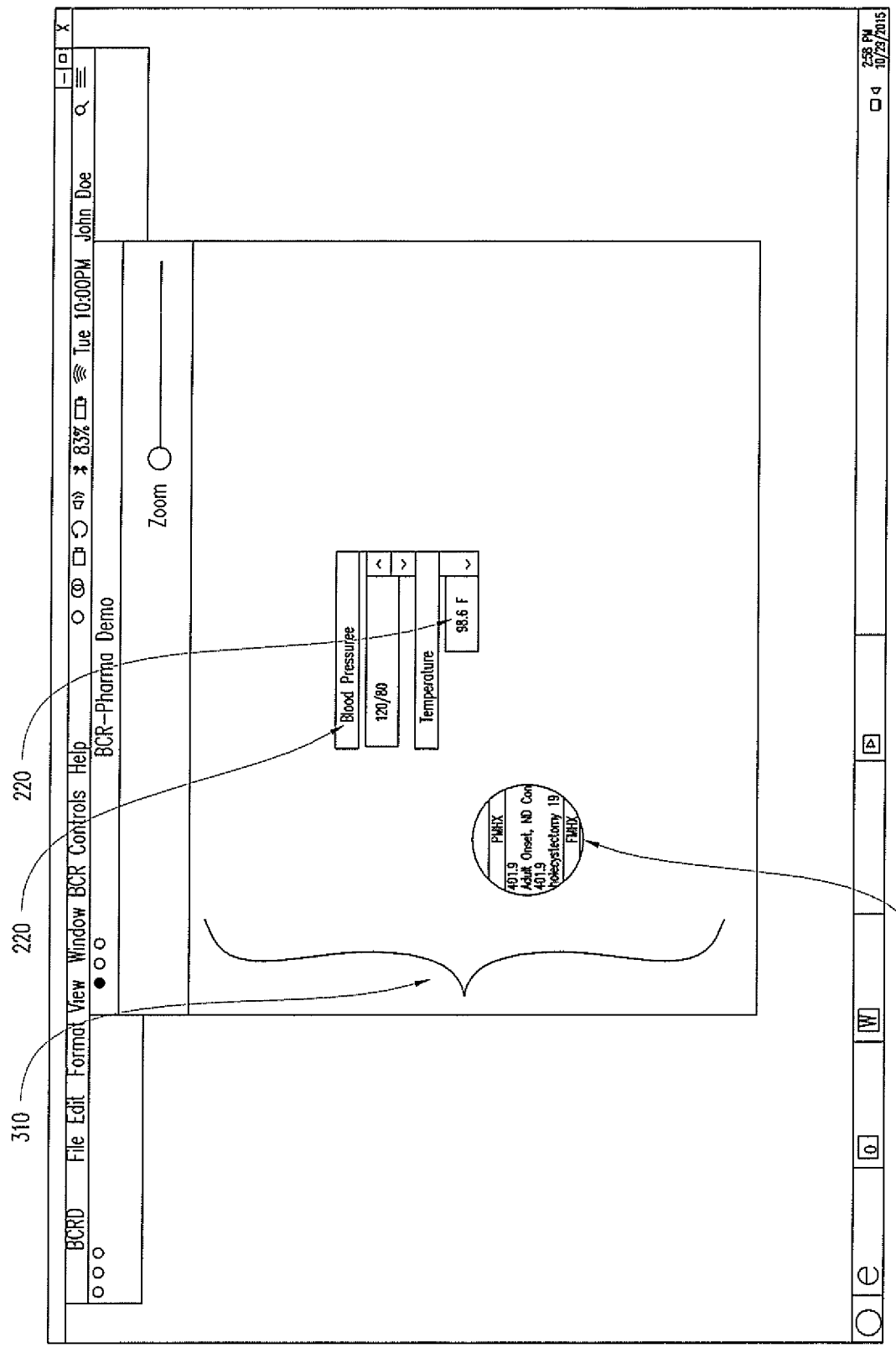
FIG. 4 is a diagram of a user interaction in accordance with an exemplary embodiment of the present invention.

Referring to FIG. 3, in an exemplary embodiment, the present invention allows a pharmaceutical company (Sponsor) to view a redacted page 310 of the SD medical record 210, where only the information relevant to the study 220 is shown with the rest of the document redacted. Referring to FIG. 4, in an exemplary embodiment, the present invention allows an authorized user to view otherwise redacted information 410 via a "viewport" tool.

Electronic Data Document

In an exemplary embodiment, the present invention provides an electronic data document (EDD) for use in a computerized clinical trial verification system. In an exemplary embodiment, the EDD includes (1) first computer instructions associated with the EDD that permit a receiver of the EDD to validate a sender of the EDD and an electronic data structure of the EDD, (2) an image of a source document (SD) that comprises a record of at least one interaction between a clinical trial investigator and a patient enrolled in a clinical trial, (3) at least one revealed portion of the SD that comprises evidence relevant to at least one question in a clinical trial questionnaire, and (4) at least one marking connecting the revealed portion to the at least one question.

In a further embodiment, the EDD further includes second computer instructions associated with the EDD that mask all portions of the SD not included in the revealed portion and that permit authorized persons to selectively unmask one or more portions of the SD that are not included in the revealed portion. In a further embodiment, the EDD further includes third computer instructions that permit one or more authorized persons to accept the revealed portion as sufficient evidence to answer the at least one question.

In a further embodiment, the EDD further includes at least one question from the clinical trial questionnaire. For example, one of the questions from the questionnaire could be part of the EDD (e.g., what is the patient's blood pressure?). In such an example, the "answer" to that question would be the revealed portion of the SD that includes evidence relevant to at least one question in the clinical trial questionnaire (which shows the entry for the blood pressure). Also, in such an example, the marking that is dragged on and associated with the revealed portion (e.g., "Blood pressure") would link the question to the revealed portion (the "evidence"). In an exemplary embodiment, the EDD includes questions that are automatically superimposed on the SD, such that the investigator could reveal relevant portions of the SD to answer the questions.

In an exemplary embodiment, the EDD is encrypted. In a further embodiment, the EDD further includes fourth computer instructions that permit the investigator to associate an electronic signature with the EDD, thereby allowing the investigator to note that the EDD is truthful and representative of the patient, dates, and information submitted in response to the clinical trial questionnaire. In a further embodiment, the EDD further includes fifth computer instructions that permit the investigator to associate an electronic signature with the revealed portion, thereby allowing the investigator to note that the revealed portion is truthful and representative of the patient and of dates associated with the revealed portion.

Computerized System

Figure 5:
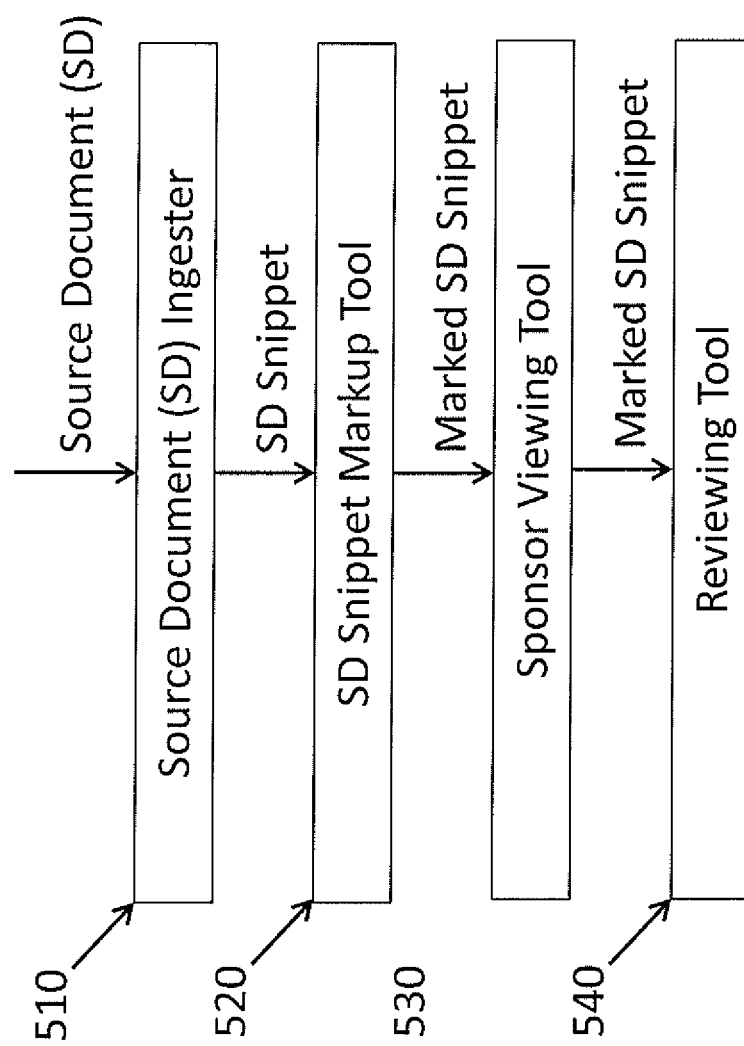
FIG. 5 is a diagram of a computerized system in accordance with an exemplary embodiment of the present invention.

Referring to FIG. 5, in an exemplary embodiment, the present invention provides a computerized system for allowing at least one medical professional (Investigator) to answer questions from a clinical trial questionnaire (case report form (CRF)) pertinent to a clinical trial of a medical treatment. In an exemplary embodiment, the system includes a source document (SD) ingester 510 configured to allow the Investigator to answer the questions with digital photographs of portions of the SD (SD snippets) as evidence for answers to the questions, where the SD includes a description of at least one interaction between the Investigator and a patient enrolled in the clinical trial (Subject), a SD snippet markup tool 520 configured to allow the Investigator to annotate SD snippets 220, thereby allowing the Investigator to draw attention of the Sponsor to information relevant to the clinical trial via annotated SD snippets, a sponsor viewing tool 530 configured to allow a manufacturer of the medical treatment (Sponsor) to view the SD snippets and the annotated SD snippets (SD snippet images), and a reviewing tool 540 configured to allow the Sponsor to accept the SD snippet images if the SD snippet images are supportive and are representative of the answers to the questions and to reject the SD snippet images if the SD snippet images are not supportive and are not representative of the answers to the questions. In an exemplary embodiment, the description includes alphanumeric characters written or typed by the Investigator.

In an exemplary embodiment, each of the snippets 220 are digital photographs or an output of an imaging device, where the imaging device may be a digital camera, computer screen capture software, a mobile telephone, a medical scanner or imaging machine and a portable computer. For example, if medical records are in paper form, an Investigator may take photographs of relevant medical charts of the Subject with a mobile telephone. In another exemplary embodiment, the description includes a chart or other representation of patient-related data obtained from testing the patient.

In an exemplary embodiment, SD snippet markup tool 520 includes computer software, where the computer software is selected from the group consisting of a computer software drawing tool, a computer software labeling tool, mobile telephone application software configured to receive stylus input, and mobile telephone application software configured to receive touch screen input. For example, if medical records are in paper form and the Investigator has obtained SD snippets with a mobile telephone, the Investigator may mark key areas of the SD snippets via a stylus or a finger on the screen of the mobile telephone. In an exemplary embodiment, sponsor viewing tool 530 is configured to mask from viewing by the Sponsor all portions of the SD that do not correspond to the SD snippet images. In a further embodiment, sponsor viewing tool 530 is further configured to display to at least one authorized person at least one portion of the SD that does not correspond to the SD snippet images.

In a further embodiment, SD ingester 510 is further configured to allow the Investigator to capture a digital image of the entire SD (SD full image). In a further embodiment, SD ingester 510 further includes a SD full image viewing tool configured to display to at least one authorized person the SD full image. For example, authorized personnel may include federal regulators (e.g., FDA personnel), privileged quality assurance administrators of the clinical trial, or study monitors.

In a further embodiment, the system further includes an electronic signature tool configured to allow the Investigator to associate an electronic signature with the SD snippet images, thereby allowing the Investigator to note that the SD snippet images are truthful and representative of the Subject, dates, and information submitted in response to the CRF. In a further embodiment, SD ingester 510 further includes an electronic signature tool configured to allow the Investigator to associate an electronic signature with the SD full image, thereby allowing the Investigator to note that the SD full image is truthful and representative of the Subject, dates, and information submitted in response to the CRF. In an exemplary embodiment, the electronic signature includes a two token code that is kept secret by the Investigator.

Method

Figure 6A:
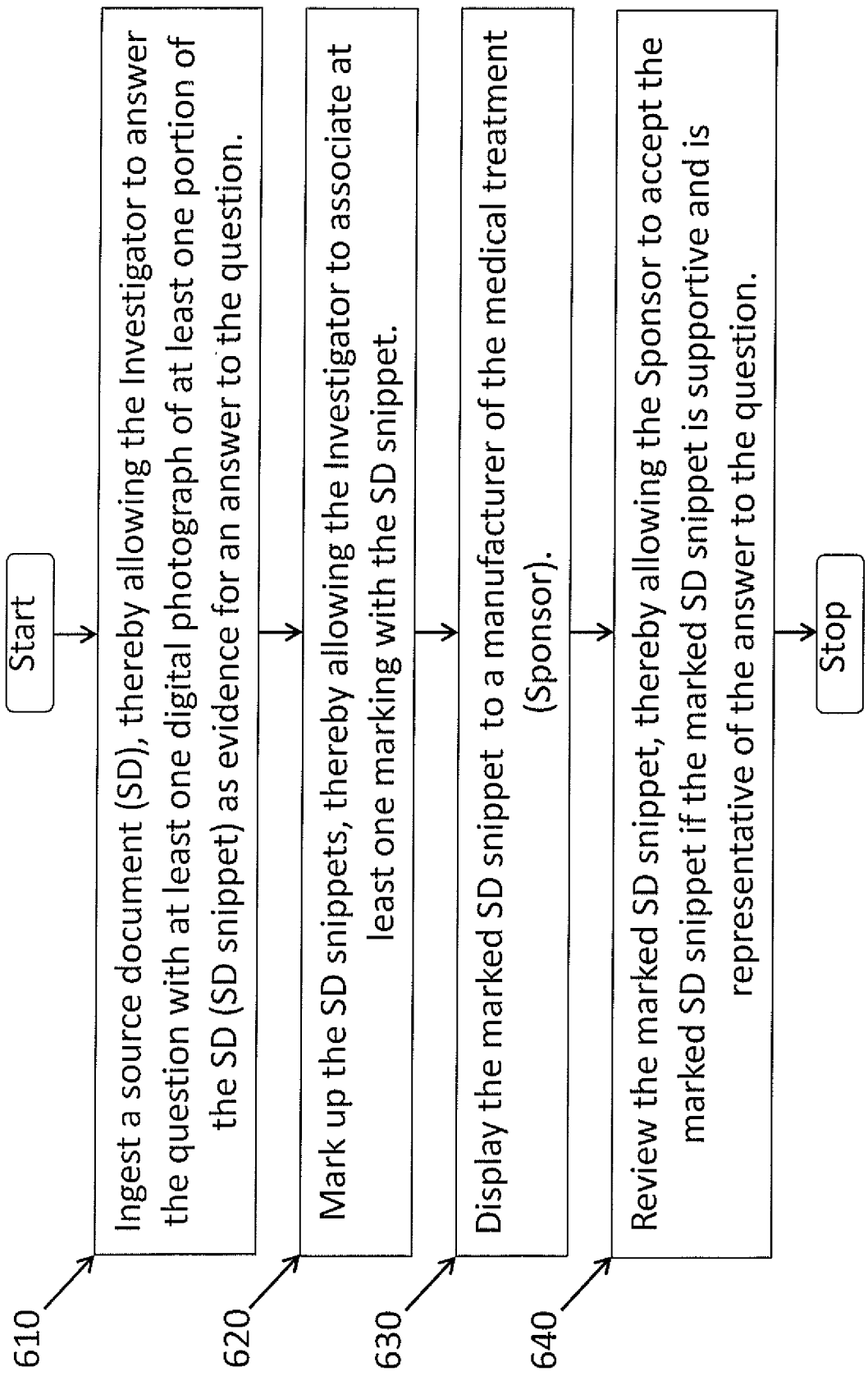
FIG. 6A is a flowchart in accordance with an exemplary embodiment of the present invention.

Referring to FIG. 6A, in an exemplary embodiment, the present invention provides a method for allowing at least one medical professional (Investigator) to answer questions from a clinical trial questionnaire (case report form (CRF)) pertinent to a clinical trial of a medical treatment. In an exemplary embodiment, the method includes a step 610 of ingesting a source document (SD), thereby allowing the Investigator to answer the questions with digital images of portions of the SD (SD snippets) as evidence for answers to the questions, wherein the SD comprises a description of at least one interaction between the Investigator and a patient enrolled in the clinical trial (Subject), a step 620 of marking up the SD snippets, thereby allowing the Investigator to mark the SD snippets 220, thereby allowing the Investigator to draw attention of the Sponsor to information relevant to the clinical trial via marked SD snippets, a step 630 of displaying SD snippets 220 and the marked SD snippets (SD snippet images) to a manufacturer of the medical treatment (Sponsor), and a step 640 of reviewing the SD snippet images, thereby allowing the Sponsor to accept the SD snippet images if the SD snippet images are supportive and are representative of the answers to the questions and to reject the SD snippet images if the SD snippet images are not supportive and are not representative of the answers to the questions.

In an exemplary embodiment, each of the digital images 220 includes an output of an imaging device, where the imaging device is selected from the group consisting of a digital camera, computer screen capture software, a mobile telephone, a medical imaging device such as an X-ray, NMR, or CT scanner, and a portable computer. For example, if medical records are in paper form, an Investigator may take photographs of relevant medical charts of the Subject with a mobile telephone.

Figure 7:
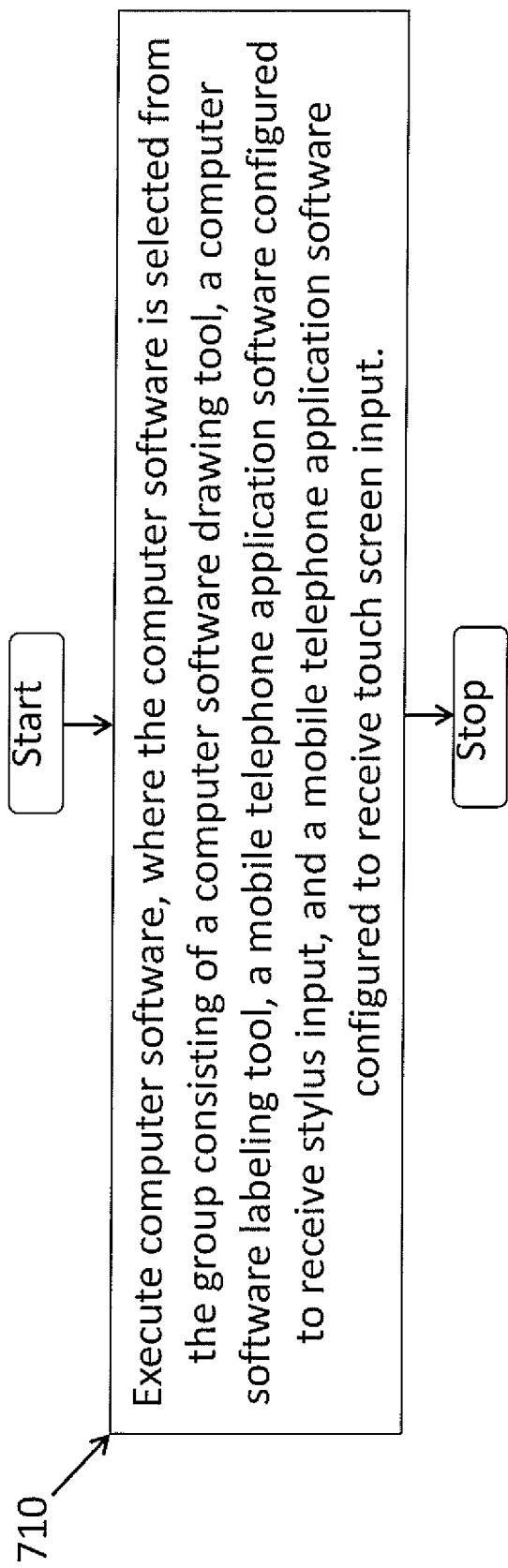
FIG. 7 is a flowchart of the marking up step in accordance with an exemplary embodiment of the present invention.
Figure 8A:
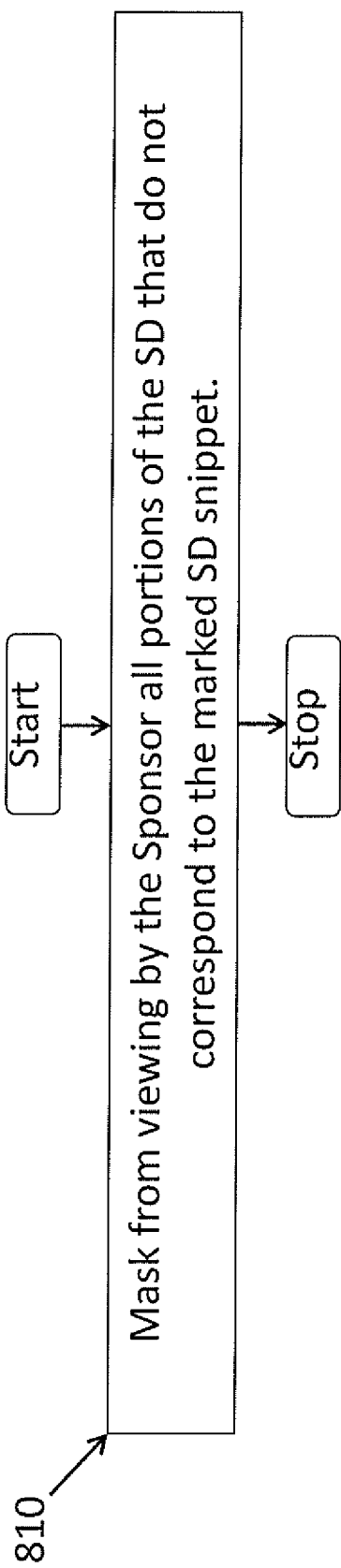
FIG. 8A is a flowchart of the displaying step in accordance with an exemplary embodiment of the present invention.
Figure 8B:
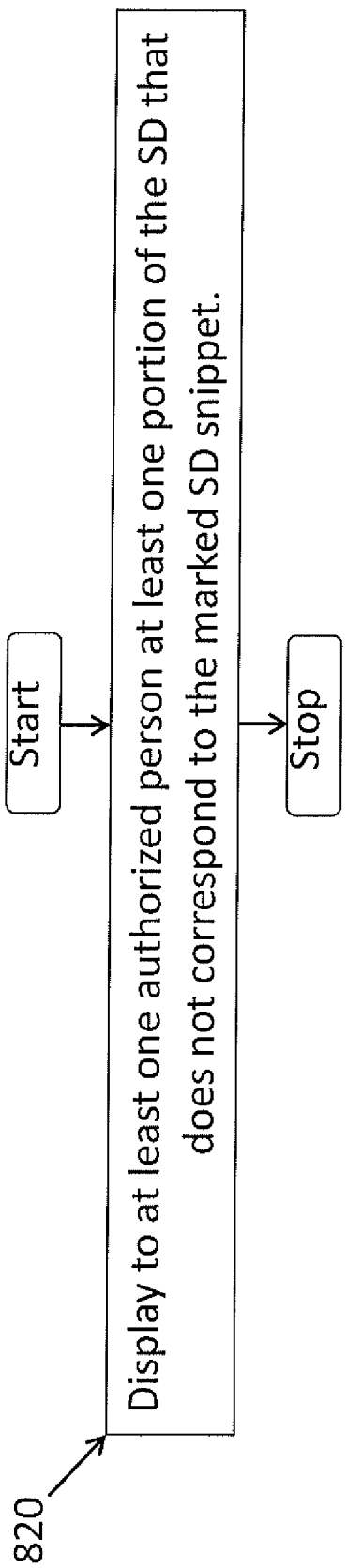
FIG. 8B is a flowchart of the displaying step in accordance with a further embodiment of the present invention.

Referring to FIG. 7, in an exemplary embodiment, marking up step 620 includes a step 710 of executing computer software, where the computer software is selected from the group consisting of a computer software drawing tool, a computer software labeling tool, a mobile telephone application software configured to receive stylus input, and a mobile telephone application software configured to receive touch screen input. Referring to FIG. 8A, in an exemplary embodiment, displaying step 630 includes a step 810 of masking from viewing by the Sponsor all portions of the SD that do not correspond to the SD snippet images. Referring to FIG. 8B, in a further embodiment, displaying step 630 further includes a step 820 of displaying to at least one authorized person at least one portion of the SD that does not correspond to the SD snippet images.

Figure 9A:
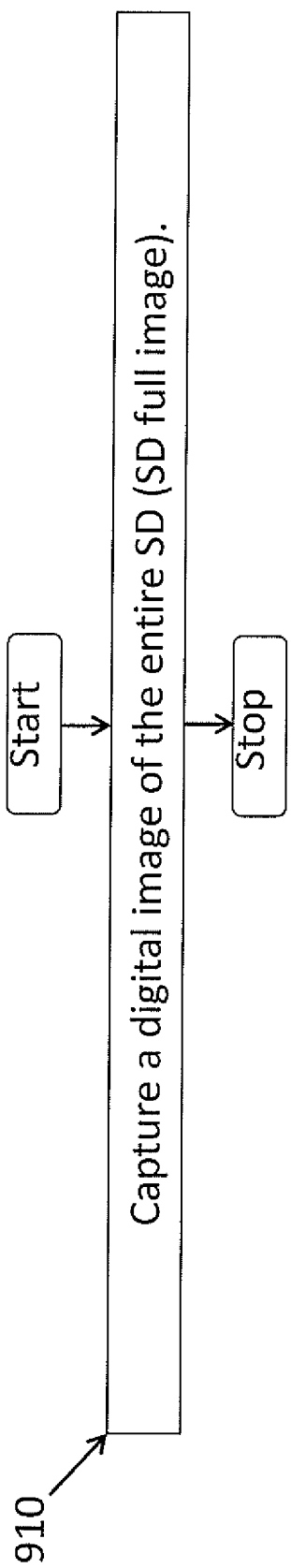
FIG. 9A is a flowchart of the ingesting step in accordance with a further embodiment of the present invention.
Figure 9B:
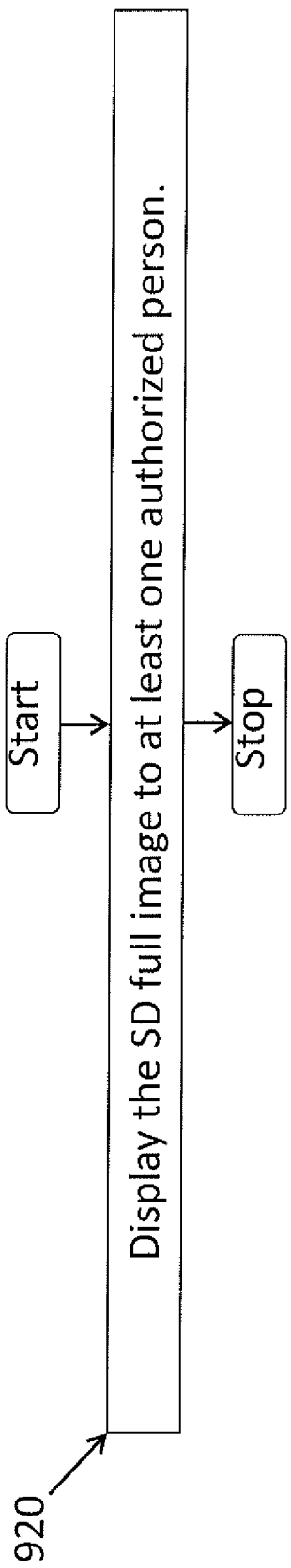
FIG. 9B is a flowchart of the ingesting step in accordance with a further embodiment of the present invention.

Referring to FIG. 9A, in a further embodiment, ingesting step 610 further includes a step 910 of capturing a digital image of the entire SD (SD full image). Referring to FIG. 9B, in a further embodiment, ingesting step 610 further includes a step 920 of displaying the SD full image or necessary parts thereof to at least one authorized person. For example, authorized personnel may include federal regulators (e.g., FDA personnel), privileged quality assurance administrators of the clinical trial, or study monitors.

Figure 6B:
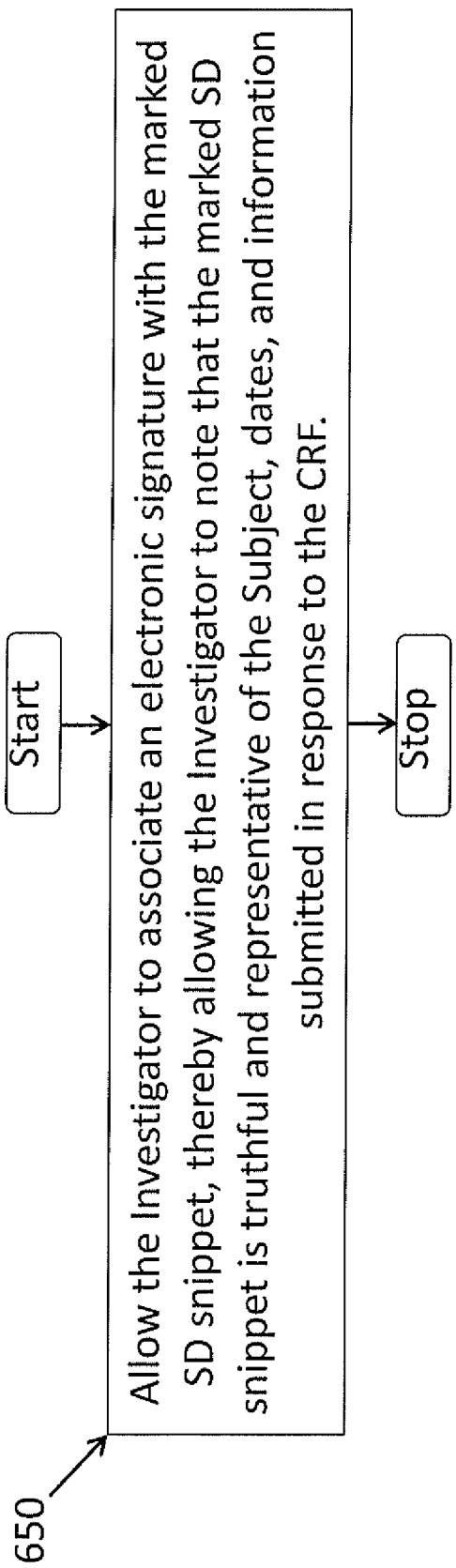
FIG. 6B is a flowchart in accordance with a further embodiment of the present invention.
Figure 10:
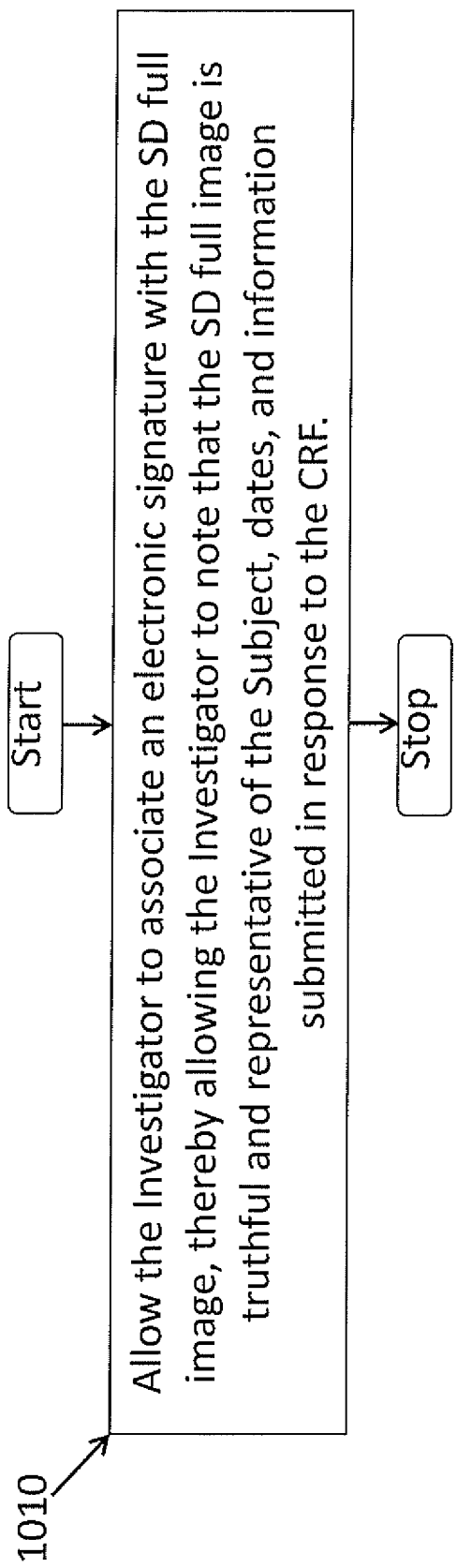
FIG. 10 is a flowchart of the ingesting step in accordance with a further embodiment of the present invention.

Referring to FIG. 6B, in a further embodiment, the method further includes a step 650 of allowing the Investigator to associate an electronic signature with the SD snippet images, thereby allowing the Investigator to note that the SD snippet images are truthful and representative of a particular Subject, dates, and information submitted in response to the CRF. Referring to FIG. 10, in a further embodiment, ingesting step 610 further includes a step 1010 of allowing the Investigator to associate an electronic signature with the SD full image, thereby allowing the Investigator to note that the SD full image is truthful and representative of the Subject, dates, and information submitted in response to the CRF.

General

The present invention can take the form of an entirely hardware embodiment, an entirely software embodiment, or an embodiment containing both hardware and software elements. In an exemplary embodiment, the present invention is implemented in software, which includes but is not limited to firmware, resident software, and microcode. Any conventional EMR system can be used as a source of SD, such as Cerner, Epic Systems and Allscripts. Preferably, the systems and methods of the present invention are implemented in a client/server network connected via the Internet.

The systems and methods of the present invention will also preferably use data security, encryption, and data capture and transfer protocols that will enhance patient privacy and security and add desirable authentication and verification features. Preferably, all data will be transferred over SSL connections (also known as HTTPS). Preferably, the systems and methods of the invention will use data encryption (public/private key pair) to protect patient medical records represented in SD media, and data encryption will protect both data and media while they are stored and while they are being transferred, ensuring that only the intended recipients are able to access/view them. Preferably, every user must be authenticated on the system by logging in with their private credentials. Preferably, during each interaction with the server, the server confirms the authenticity of the request for interaction by authentication tokens issued by the server. Preferably, the system will require the users to change their passwords periodically. Preferably, users will only have access to the functionality assigned to them by the system administrator. Preferably, information such as patient or subject ID, data capture date, and other necessary identifying information is embedded in the SD image itself as well as included in metadata, and accessible to qualified users and viewers of the SDD In another preferred embodiment, no media or data is saved to any local machine or device, either by the machine or device as it is created or by the Sponsor or Investigator when viewing it. Rather, data is captured directly from the screen output by the inventive software and is not handled by the native Operating System, which might write that data to disk, even if only as temporarily cached files. Any additional image processing that may be required, such as file compression for storage, is handled by servers away from the local machine or device. Preferably, the computer systems and programs used in embodiments of the invention do not save the SDD or other files created incident to the operation of the invention as a file that can be recalled at a later time. Screenshot captures can be obtained from any EMR software running on the same machine as the inventive software, such that the EMR software displays its information on the same screen(s) as are accessible by software implementing the invention. Additional digital media imported by the invention from any external source, such as photographs of paper documents or medical scans, are treated in the same manner as screenshot captures once loaded.

Furthermore, the present invention can take the form of a computer program product or products accessible from a computer-usable or computer-readable medium providing program code for use by or in connection with a computer system or any instruction execution system. The computer program product includes the instructions that implement the method of the present invention. A computer-usable or computer readable medium can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid-state memory, magnetic tape, a removable computer diskette, a random access memory (RAM), a read-only memory (ROM), a rigid magnetic disk, and an optical disk. Current examples of optical disks include compact disk-read only memory (CD-ROM), compact disk-read/write (CD-R/W), and DVD.

A computer system suitable for storing and/or executing program code includes at least one processor coupled directly or indirectly to memory elements through a system bus. The memory elements include local memory employed during actual execution of the program code, bulk storage, and cache memories that provide temporary storage of at least some program code to reduce the number of times code is retrieved from bulk storage during execution. Input/output (I/O) devices (including but not limited to keyboards, displays, pointing devices, etc.) can be coupled to the computer system either directly or through intervening I/O controllers. Network adapters may also be coupled to the computer system in order to enable the computer system to become coupled to other computer systems or remote printers or storage devices through intervening private or public networks. Modems, cable modems, and Ethernet cards are just a few of the currently available types of network adapters. The computer system can also include an operating system and a computer file-system.

It is to be understood that the above description and examples are intended to be illustrative and not restrictive. Many embodiments will be apparent to those of skill in the art upon reading the above description and examples. The scope of the invention should, therefore, be determined not with reference to the above description and examples, but should instead be determined with reference to the appended claims, along with the full scope of equivalents to which such claims are entitled. The disclosures of all articles and references, including patent applications and publications, are incorporated herein by reference for all purposes.

What is claimed is:

1. An electronic data document (EDD) in a non-transitory computer-readable medium for use in a computerized clinical trial verification system, the system comprising a first computer program that can be used by a clinical trial investigator to create the EDD and a second computer program that can read and modify the EDD, the EDD comprising:

integrated computer instructions that are compatible with the first computer program and the second computer program and integrated with the EDD;

at least one screenshot capture obtained directly from a source document (SD) for an official electronic medical records system (EMR), wherein the screenshot capture consists of at least a portion of the source document, wherein one or more parts of the at least one screenshot capture are used as supportive evidence to answer at least a portion of at least one question from a clinical trial questionnaire;

wherein the integrated computer instructions further comprise:

first computer instructions that permit a receiver of the EDD to validate a sender of the EDD and an electronic data structure of the EDD;

second computer instructions that permit information to be selected and labeled in the screenshot capture for use as supportive evidence for answering at least a portion of the at least one question from a clinical trial questionnaire; and third computer instructions that permit one or more authorized users of the second computer program to modify the EDD to show that the selected and labeled information of the screenshot capture is acceptable evidence to answer the at least one question from the clinical trial questionnaire;

fourth computer instructions that mask from view by the receiver all of the information all of the information not selected and labeled in the screenshot capture, such that the receiver can view only the selected and labeled information in the screenshot capture and the masked information is retained as part of a redacted screenshot capture; and fifth computer instructions that permit the one or more authorized users of the second computer program to selectively view one or more parts of the redacted screenshot capture.

2. The EDD of claim 1, wherein the EDD is encrypted using a public/private key pair.

3. The EDD of claim 1, wherein the computer instructions further comprise sixth computer instructions that permit the clinical trial investigator to modify the EDD to associate an electronic signature with the EDD.

4. The EDD of claim 1, wherein the second computer cannot save a copy of the EDD locally as a file that can be recalled at a later time.

5. The EDD of claim 1, wherein the computer instructions further comprise seventh computer instructions that permit the clinical trial investigator to modify the EDD to associate an electronic signature with the selected and labeled information of the at least one screenshot.

6. The EDD of claim 1, wherein each of the questions of the clinical trial questionnaire has at least one screenshot capture as supportive evidence for an answer.

7. The EDD of claim 1, wherein the patient ID or other additional patient information is embedded in the screenshot capture of the SD.

8. The EDD of claim 1 further comprising additional digital media imported from an external source.

9. The EDD of claim 5, wherein the additional digital media consists of a photograph of a paper document or a medical scan, or other information that cannot be captured with a screenshot.

10. The EDD of claim 1, wherein the at least one screenshot capture contains only relevant data for use as supportive evidence for answering at least a portion of the at least one question.

11. The EDD of claim 1, wherein the computer instructions further comprise eighth computer instructions that automatically superimpose the at least one question from a clinical trial questionnaire on the source document.

12. The EDD of claim 1, wherein the at least one screenshot capture is obtained from any EMR software running on the system compromising the first computer program.

* * * * *